(12) United States Patent
Baus

(10) Patent No.: US 6,483,119 B1
(45) Date of Patent: Nov. 19, 2002

(54) ULTRAVIOLET TREATMENT FOR LIQUID DISPENSING UNIT

(76) Inventor: Wayne A. Baus, 44285 Telegraph Rd., Elyria, OH (US) 44035

( * ) Notice: Subject to any disclaimer, the term of this patent is extended or adjusted under 35 U.S.C. 154(b) by 0 days.

(21) Appl. No.: 09/404,225

(22) Filed: Sep. 23, 1999

(51) Int. Cl.[7] .............................................. G01N 21/01
(52) U.S. Cl. ...................... 250/436; 250/432 R; 422/24
(58) Field of Search ........................ 422/24; 250/432 R, 250/436

(56) References Cited

U.S. PATENT DOCUMENTS

| | | | | |
|---|---|---|---|---|
| 4,276,256 A | * | 6/1981 | Karamian | 422/24 |
| 4,757,921 A | * | 7/1988 | Snowball | 250/436 |
| 5,316,673 A | * | 5/1994 | Kohlmann et al. | 210/251 |
| 5,441,179 A | * | 8/1995 | Marsh | 222/190 |
| 5,900,212 A | * | 5/1999 | Maiden et al. | 250/432 R |
| 6,139,726 A | * | 10/2000 | Greene | 250/436 |

* cited by examiner

*Primary Examiner*—Bruce Anderson
(74) *Attorney, Agent, or Firm*—Barbara Joan Haushalter

(57) ABSTRACT

A system and method are provided for treating liquids in a dispensing reservoir. An ultraviolet source is located in a liquid dispensing reservoir or well. The ultraviolet source discharges ultraviolet light rays in the dispensing reservoir to treat the liquid by killing bacteria in the liquid. One or more existing or added baffle means prevent the ultraviolet light rays from being emitted outside of the dispensing reservoir. The ultraviolet source comprises a waterproof submersible element, with a transformer and a ground fault interrupter breaker typically located outside the reservoir.

9 Claims, 3 Drawing Sheets

ULTRAVIOLET TREATMENT FOR LIQUID DISPENSING UNIT

BACKGROUND OF THE INVENTION

The present invention relates to liquid dispensing units and, more particularly, to an ultraviolet device for use within a liquid dispenser such as a bottle water receiving and dispensing reservoir to kill bacteria.

Bottles are used to transport and store many liquid materials, including water, milk, and other beverages. In the bottled water industry, for example, bottles are used to transport bottled water to various locations and to provide a dispensing unit for storing and dispensing the water. Bottled water is an attractive alternative to tap water and its use is widespread for many reasons. Bottled water dispensing units can dispense water at home, in the workplace, and in the marketplace for drinking and cooking without the need for a plumbed water system. Recreational vehicle users and campers find bottled water to be a convenient water source while away from home and plumbed water sources.

When the liquid is transported to a dispensing site, for example in the case of bottled water, the water is released from the transporting jug (which is sterile to prevent bacteria from mixing with the water), into a dispensing reservoir or chiller well. However, the reservoir is not within the control of the bottled water providing service, and therefore typically not subject to nor maintained at the same stringent sterility requirements of the original bottle or jug of water. If the well does not meet the bacteria-free level required of the dispensing jug, or cannot be confirmed to be at a desired bacteria-free level, all of the care taken to avoid bacteria in the bottled water is for naught, once the bottled water is dispensed into the dispensing reservoir. Obviously, this is true anytime a liquid is released from a controlled environment into lesser controlled environment for dispensing purposes. There is no existing means in the current art for purifying water at the dispenser or well unit.

It is seen then that there exists a need for a means for eliminating undesirable bacteria levels which can collect in a liquid dispenser unit or well.

SUMMARY OF THE INVENTION

This need is met by the technique according to the present invention, wherein an ultraviolet device is used in any existing liquid dispenser reservoir or well, including bottled water dispensing units with or without a cooling means, to kill certain of the bacteria that can contaminate the liquid. The ultraviolet device is effective without the need for retrofit.

In accordance with one aspect of the present invention, an ultraviolet device is located to kill bacteria in a liquid dispensing reservoir. The ultraviolet device preferably comprises a waterproof submersible element, with a transformer to generate necessary power and a ground fault interrupter breaker as a safety device. The ultraviolet device can be anchored to or otherwise associated with an existing baffle already in the well, allowing the baffle plate to prevent any ultraviolet rays from exiting the well. Alternatively, a baffle or floating baffle can be added, used alone, or used in conjunction with an existing baffle, to prohibit the escapement of the ultraviolet rays from the reservoir.

Other objects and advantages of the invention will be apparent from the following description, the accompanying drawings and the appended claims.

DETAILED DESCRIPTION OF THE PREFERRED EMBODIMENTS

Figure 1:
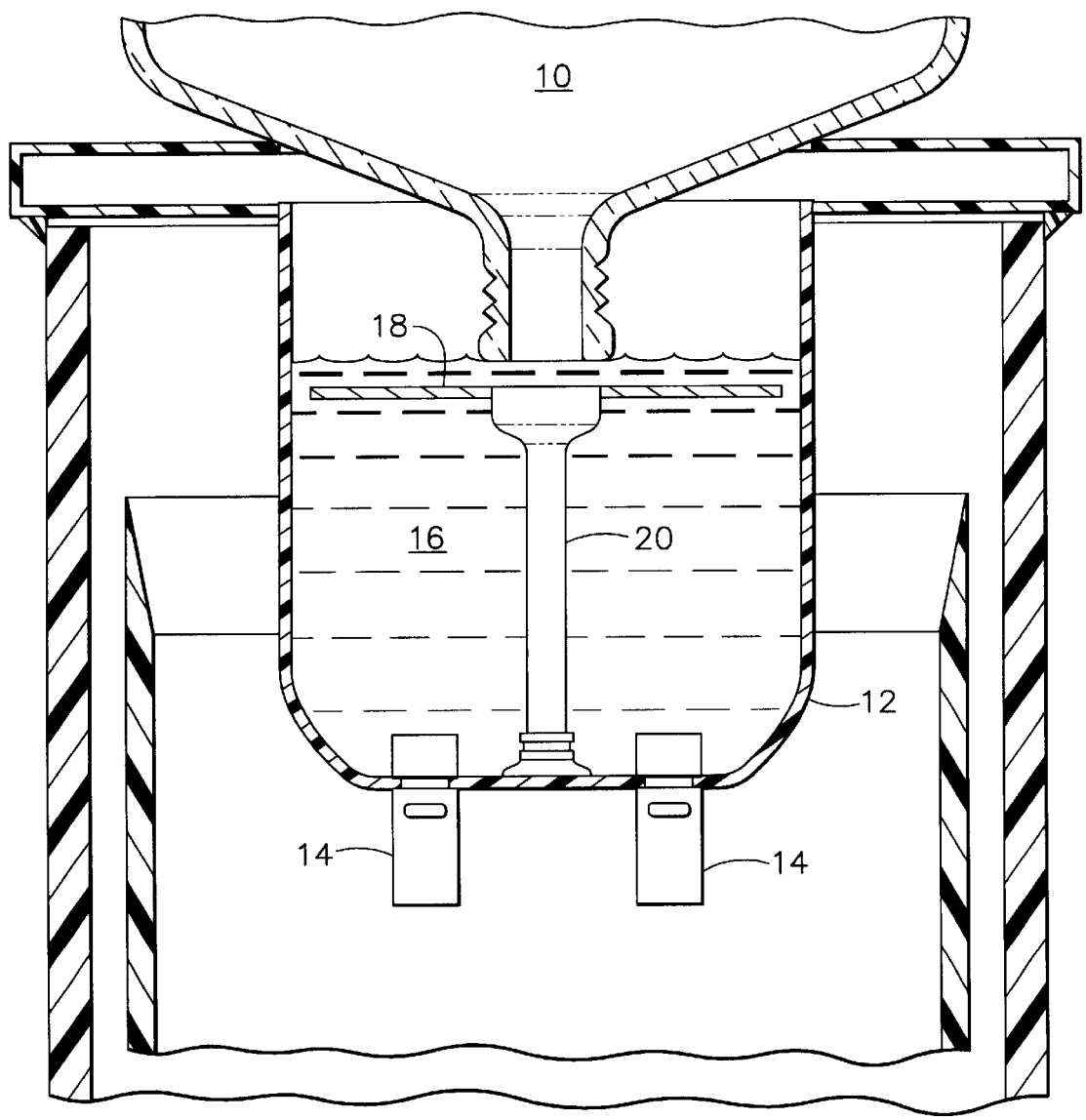
FIG. 1 is a front view of a typical bottle water or other liquid dispensing unit.

The present invention provides a means and method for treating liquid such as bottled water when the liquid is contained in a dispensing chiller or reservoir. Currently, water or other liquid is transported to dispensing sites in sterile bottles, jugs, or other suitable means. The jug 10 dispenses liquid into the dispensing unit 12. The dispensing unit typically has one or two spigots 14 for dispensing room temperature and/or chilled liquid or water 16. A baffle plate 18 is used to draw water off and cool the water at a certain rate. Water from the jug 10 is retained in reservoir 12 at a level where the neck of the bottle touches the water. The water spills into and around the baffle and is drawn out from under the baffle to tubing 20, which is connected to spigots 14 for dispensing the water as needed. When the water 16 level in reservoir 12 gets below the baffle plate 18, and the jug 10 is empty, a new full jug 10 is inserted to supply more water.

The problem addressed by the present invention is the issue of bacteria in the liquid. The invention is described herein using bottled water as the exemplary liquid. However, it will be obvious to those skilled in the art that the ultraviolet treatment of the present invention is applicable to many forms of flowing liquid. Therefore, the reference to water is not to be considered as limiting the scope of the invention.

Bottled water preferably adheres to stringent requirements to kill bacteria, thereby providing clean, healthy drinking water. These standards can be maintained with respect to the water in the jug 10, as the jug 10 is filled in a controlled environment where the standards can be monitored and maintained. However, the dispensing unit 12 is not usually within the possession and control of the bottle water supplier. Therefore, bacteria in the dispensing unit 12 can contaminate the water from the jug 10, as the water enters the dispensing unit. The present invention proposes the application of ultraviolet treatment to the water in the reservoir 12 to kill bacteria and thereby maintain the level of sterility preferred for the water as the water leaves the jug 10 and enters the dispensing unit 12.

In accordance with the present invention, a source of ultraviolet light is used within the reservoir 12. The ultraviolet device has the advantage of being applicable for use on existing dispensing units without the need for modification or retrofit of the unit. The ultraviolet source may be located anywhere in or around the area of the dispensing unit 12. It will be obvious to those skilled in the art that the location of the ultraviolet source can be any one or more of multiple locations without departing from the spirit of the invention, with the location being suitable to permit treating of the treatment area, where the treatment area is the well area of dispenser 12.

Figure 2:
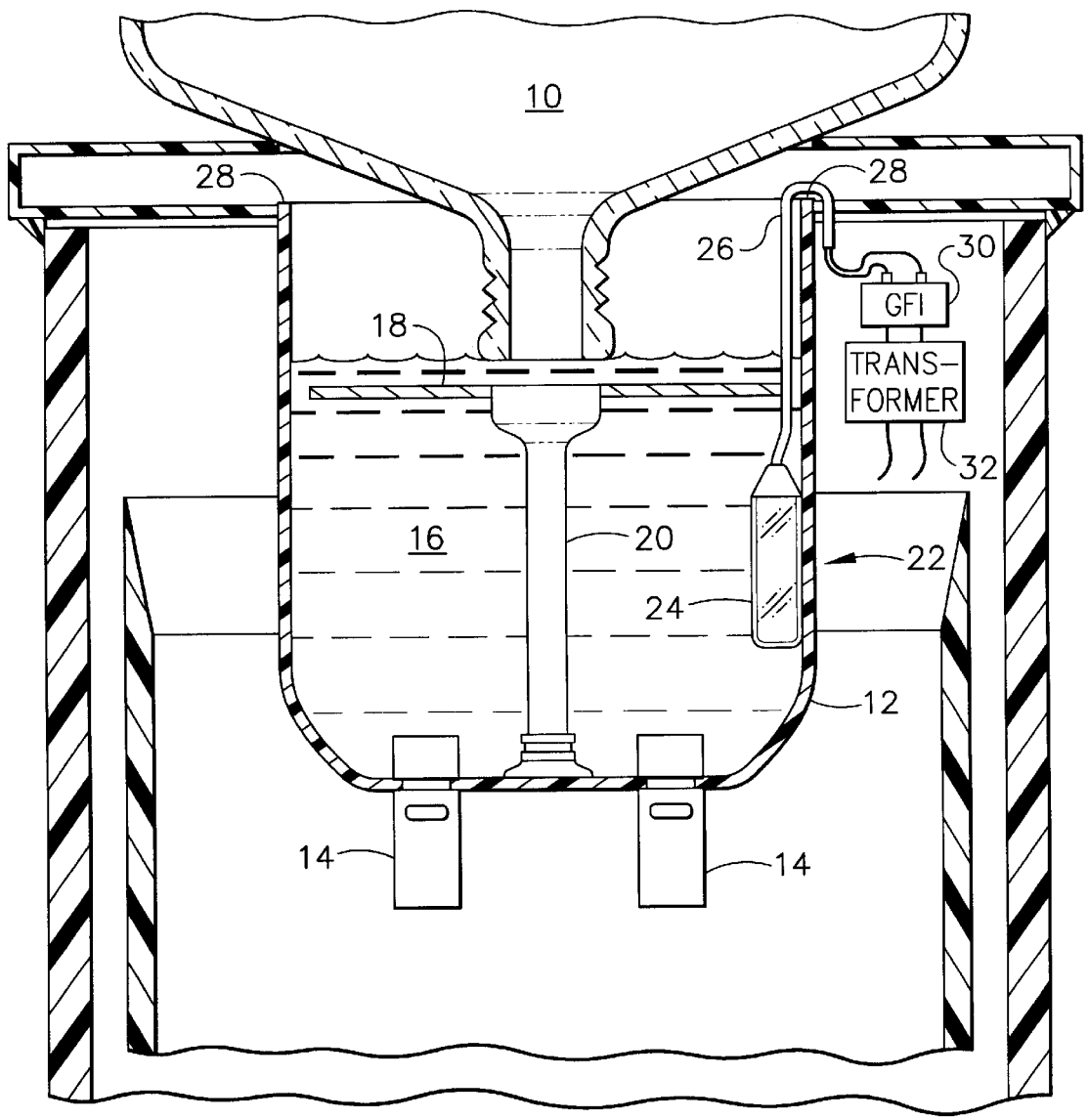
FIG. 2 is a front view of the liquid dispensing unit of FIG. 1 incorporating the ultraviolet treatment device according to one embodiment of the present invention.
Figure 3:
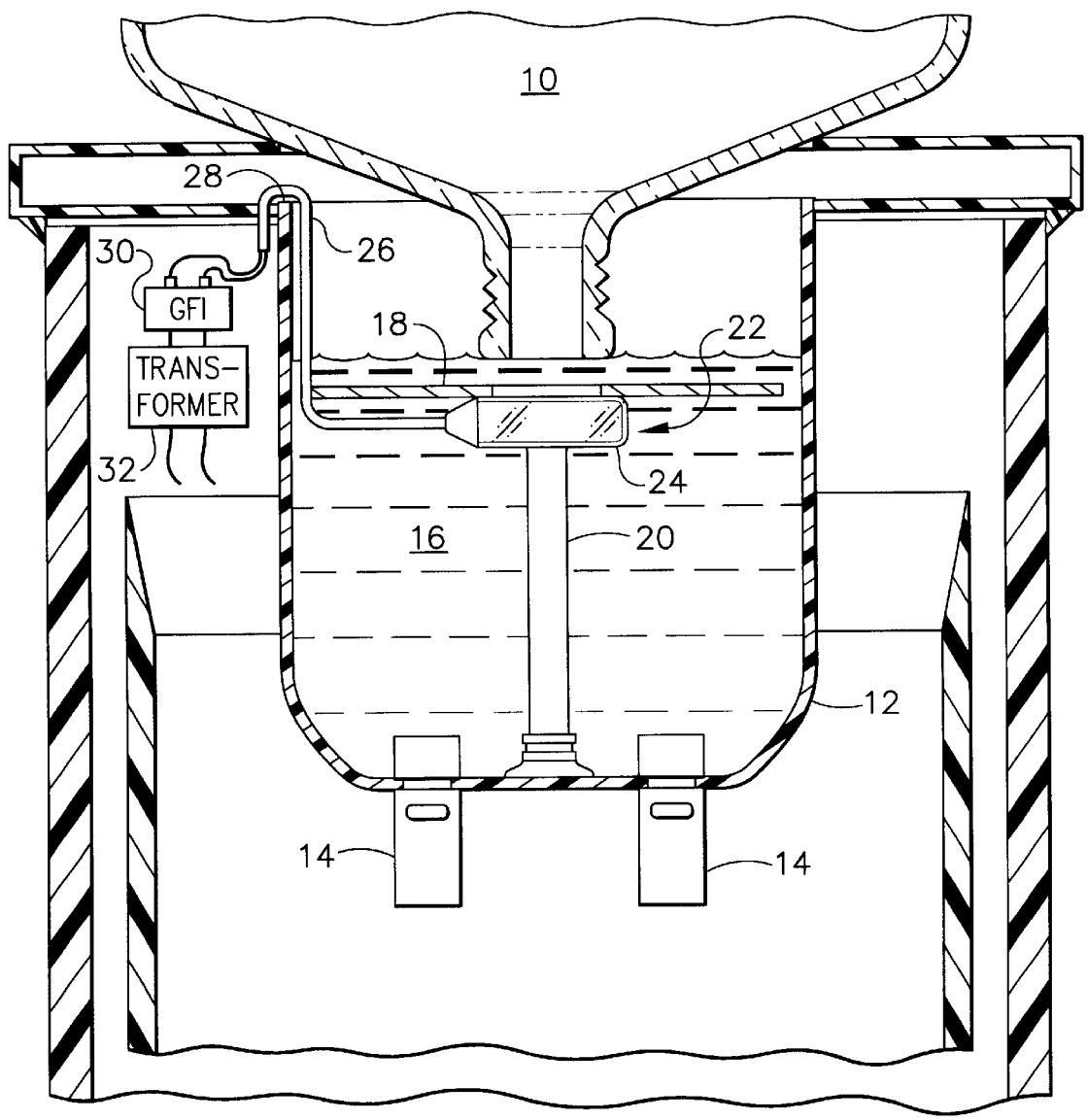
FIG. 3 is a front view of the liquid dispensing unit of FIG. 1 incorporating the ultraviolet treatment device according to an alternative embodiment of the present invention.

Without intending to limit the scope of the invention, two of the multiple possible locations for the ultraviolet source are illustrated in FIGS. 2 and 3. FIG. 2, for example, shows the ultraviolet source 22 with a bulb 24 suspended from the top of the reservoir 12. The bulb 12 is supported and held in position by hooking supporting means 26 over the rim 28 of the reservoir 12. The supporting means can comprise any material with power protection, that can be submersed in the liquid. The supporting means 26 is attached to a GFI breaker 30 and transformer 32, which can be located anywhere in or around the dispenser unit.

An alternative embodiment for placement of the ultraviolet source is illustrated in, FIG. 3. Again, a supporting means 26 allows, at one end, the ultraviolet source to be positioned to kill bacteria in the water and, at the other end, to be connected to the GFI breaker 30 and transformer 32. In this embodiment, the ultraviolet source is anchored to an existing or added baffle device, with the bulb 24 fastened to the underside of the baffle plate 18. In this embodiment, then, the rim 28 is not required to support the bulb 24.

Multiple alternative embodiments for placement of the bulb will occur to those skilled in the art. In a preferred embodiment, the bulb 24 will operate continuously while the water cooler or reservoir is in operation. The bulb apparatus can be equipped with spade connectors on the connecting wire for quick and easy bulb replacement.

When the reservoir 12 is equipped to adjust and provide various temperatures of the water 16, the intake for the hot water tank can be located just under baffle plate 18 to insure treatment of all hot and cold water. Also, in the case of a cook and cold, the water intake will always be located beneath a baffle. The baffle prevents ultraviolet rays from being emitted outside of the well area. The baffle can fasten or float in close proximity to the well to prevent the emission of ultraviolet while permitting water to pass. The ultraviolet source can even be secured to the baffle. A baffle can be added to the system, or an existing baffle can be used alone or in conjunction with the additional baffle, to prevent the escapement of ultraviolet rays from the reservoir.

Having described the invention in detail and by reference to preferred embodiments thereof, it will be apparent that other modifications and variations are possible without departing from the scope of the invention defined in the appended claims.

What is claimed is:

1. A system for treating liquid in a dispensing reservoir, the system comprising:

an ultraviolet source including a waterproof submersible element having a transformer and a ground fault interrupter breaker and capable of generating power, and further including a safety mechanism;

means for locating the ultraviolet source in the dispensing reservoir to discharge ultraviolet light rays in the dispensing reservoir to treat the liquid.

2. A system as claimed in claim 1 further comprising a baffle means to prevent the ultraviolet light rays from being emitted outside of the dispensing reservoir.

3. A system as claimed in claim 2 wherein the ultraviolet source is secured to the baffle means.

4. A system as claimed in claim 1 wherein the safety mechanism comprises a ground fault interrupter breaker.

5. A system as claimed in claim 1 wherein the ultraviolet source is suspended from a rim of the dispensing reservoir.

6. A method for treating liquid in a dispensing reservoir, the method comprising the steps of:

providing an ultraviolet source including a waterproof submersible element having a transformer and a ground fault interrupter breaker and capable of generating power, and further including a safety mechanism;

locating the ultraviolet source in the dispensing reservoir;

discharging ultraviolet light rays from the ultraviolet source in the dispensing reservoir to treat the liquid.

7. A method as claimed in claim 6 further comprising the step of using a baffle means to prevent the ultraviolet light rays from being emitted outside of the dispensing reservoir.

8. A method as claimed in claim 6 wherein the ultraviolet source is suspended from a rim of the dispensing reservoir.

9. A method as claimed in claim 6 wherein the ultraviolet source is secured to the baffle means.

* * * * *